(12) United States Patent
Saito et al.

(10) Patent No.: US 7,393,982 B2
(45) Date of Patent: *Jul. 1, 2008

(54) PROCESSES FOR PREPARING β-DIKETONE COMPOUND, METAL COMPLEX THEREOF AND METALLIC COMPOUND

(75) Inventors: Makoto Saito, Kawasaki (JP); Takashi Ueda, Kawasaki (JP); Takashi Tani, Kawasaki (JP); Keiichi Nakamura, Kawasaki (JP)

(73) Assignee: Show A Denko K.K., Tokyo (JP)

( * ) Notice: Subject to any disclaimer, the term of this patent is extended or adjusted under 35 U.S.C. 154(b) by 236 days.

This patent is subject to a terminal disclaimer.

(21) Appl. No.: 10/559,809

(22) PCT Filed: May 20, 2004

(86) PCT No.: PCT/JP2004/007210

§ 371 (c)(1),
(2), (4) Date: Dec. 8, 2005

(87) PCT Pub. No.: WO2004/110971

PCT Pub. Date: Dec. 23, 2004

(65) Prior Publication Data

US 2007/0098897 A1      May 3, 2007

(30) Foreign Application Priority Data

Jun. 10, 2003   (JP)   .............................. 2003-165200

(51) Int. Cl.
*C07C 45/72* (2006.01)
(52) U.S. Cl. ........................ 568/385; 568/388; 568/391
(58) Field of Classification Search ....................... None
See application file for complete search history.

(56) References Cited

U.S. PATENT DOCUMENTS

| 4,804,681 | A | | 2/1989 | Keller et al. |
| 5,344,992 | A | * | 9/1994 | Drewes et al. .............. 568/314 |
| 5,444,030 | A | | 8/1995 | Boettcher et al. |
| 7,084,306 | B2 | * | 8/2006 | Saito et al. .................. 568/385 |

FOREIGN PATENT DOCUMENTS

| EP | 0454623 A1 | 10/1991 |
| EP | 0454624 A1 | 10/1991 |
| EP | 0697390 A1 | 2/1996 |
| JP | 8-92149 A | 4/1996 |

OTHER PUBLICATIONS

Roy G. Gordon, et al., "New Liquid Precursors for Chemical Vapor Deposition", Materials Research Society Proceedings, Materials Research Society, Pittsburg, PA, US, vol. 495, 1998, pp. 63-68, XP001012583, ISSN: 0272-9172.

* cited by examiner

*Primary Examiner*—Sikarl A Witherspoon
(74) *Attorney, Agent, or Firm*—Sughrue Mion, PLLC

(57) ABSTRACT

Disclosed is a process for preparing a β-diketone compound such as 2,6-dimethyl-3,5-heptanedione, which comprises reacting an ester compound such as an alkyl isobutyrate with a ketone compound such as 3-methylbutanone in the presence of an alkali metal alkoxide as a catalyst. The process comprises a step 1 in which an ester compound $CR^1R^2R^3COOQ$ is reacted with a ketone compound $CR^4R^5R^6COCH_2R_7$ using an alkali metal alkoxide catalyst to give a β-diketone compound $CR^1R^2R^2R^3COCHR^4R^5R^6$. (In the formulae, $R^7$ is hydrogen or an alkyl group of 1 to 4 carbon atoms while others are each independently hydrogen or an alkyl group of 1 to 3 carbon atoms, and at least one of $R^1$ to $R^6$ is hydrogen.)

10 Claims, No Drawings

PROCESSES FOR PREPARING β-DIKETONE COMPOUND, METAL COMPLEX THEREOF AND METALLIC COMPOUND

This application is the national stage of PCT/JP04/07210 filed May 20, 2004, and published as WO2004/110971 on Dec. 23, 2004.

FIELD OF THE INVENTION

The present invention relates to a process for preparing a β-diketone compound that is useful as a ligand of a volatile organometallic complex used as, for example, a starting material of MOCVD (metalorganic chemical vapor deposition), and more particularly to a process for preparing 2,6-dimethyl-3,5-heptanedione (sometimes abbreviated as DMHD).

The present invention also relates to a process for preparing a 2,6-dimethyl-3,5-heptanedione metal complex using the 2,6-dimethyl-3,5-heptanedione, and to a process for producing a metal or a metallic compound using the metal complex.

BACKGROUND OF THE INVENTION

As a process for the production of inorganic or metal thin films, MOCVD has been widely applied, and as MOCVD materials, metal alkoxides, β-diketone complexes, etc. have been developed. Of these, 2,2,6,6-tetramethyl-3,5-heptanedione and 2,6-dimethyl-3,5-heptanedione are known to form volatile complexes together with relatively many kinds of metals, but these compounds have not become so widespread industrially because they are expensive.

A process using Claisen condensation is well known as a process for preparing the 2,2,6,6-tetramethyl-3,5-heptanedione. For example, in J. Am. Chem. Soc., 66, 1220 (1944), ethyl pivalate is reacted with pinacolone (3,3-dimethyl-2-butanone, tert-butyl methyl ketone) using a sodium amide catalyst to synthesize 2,2,6,6-tetramethyl-3,5-heptanedione in a yield of 28%. In this literature, acylation reaction of methyl ketone with an ester using sodium ethoxide is also described, and it is reported that the reactivity is inferior when a higher ester is used.

In J. Org. Chem., 27, 1036 (1962), methyl pivalate is reacted with pinacolone using a sodium hydride catalyst to synthesize 2,2,6,6-tetramethyl-3,5-heptanedione in a yield of 60 to 70%.

Other examples of the process for preparing 2,6-dimethyl-3,5-heptanedione using Claisen condensation reaction have also been reported (Bull. Inst. Chem. Res. Kyoto Univ., vol. 46, No. 6,256 (1968) and Mat. Res. Soc. Symp. Proc., vol. 495, 63 (1998)). In any of these processes, however, sodium hydride or sodium amide that is difficult to handle similarly to the metallic sodium is used as a catalyst, and there resides a problem of safety. Moreover, safety countermeasures thereto are necessary, and hence, it is difficult to use these processes industrially.

In addition to the above processes, a synthesis process using Grignard reaction of malonyl chloride with t-BuMgCl (t-Bu is a tert-butyl group) and a synthesis process using a reaction of malonyl chloride with t-BuCu(Li)SPh have been reported. In these processes, however, an extremely low temperature of about −70° C. is necessary, and handling is very difficult. Thus, there are problems in the industrial practice.

As described above, any industrially advantageous process wherein 2,6-dimethyl-3,5-heptanedione can be prepared by simple and easy operations at a low cost has been unknown so far, and further improvement has been desired.

OBJECT OF THE INVENTION

It is an object of the present invention to provide an industrially advantageous process wherein a β-diketone compound represented by the following formula (3) can be obtained:

$$CR^1R^2R^3COCHR^7COCR^4R^5R^6 \qquad (3)$$

wherein $R^1$ to $R^6$ are each independently hydrogen or an alkyl group of 1 to 3 carbon atoms and at least one of $R^1$ to $R^6$ is hydrogen, and $R^7$ is hydrogen or an alkyl group of 1 to 4 carbon atoms.

Particularly, it is an object of the present invention to provide an industrially advantageous process wherein 2,6-dimethyl-3,5-heptanedione can be obtained easily and at a low cost.

More specifically, it is an object of the invention to provide a process wherein an alkali metal alkoxide catalyst can be used for the reaction of an ester compound represented by the formula (1):

$$CR^1R^2R^3COOQ \qquad (1)$$

wherein $R^1$ to $R^3$ are each independently hydrogen or an alkyl group of 1 to 3 carbon atoms, and Q is an alkyl group, with a ketone compound represented by the formula (2):

$$CR^4R^5R^6COCH_2R^7 \qquad (2)$$

wherein $R^4$ to $R^6$ are each independently hydrogen or an alkyl group of 1 to 3 carbon atoms, and $R^7$ is hydrogen or an alkyl group of 1 to 4 carbon atoms, to prepare the β-diketone compound represented by the formula (3), particularly the 2,6-dimethyl-3,5-heptanedione.

That is to say, it is an object of the invention to provide a process wherein an alkali metal alkoxide can be used as a catalyst for preparing 2,6-dimethyl-3,5-heptanedione from an alkyl isobutyrate and 3-methylbutanone as starting materials.

It is another object of the invention to provide a process for preparing a 2,6-dimethyl-3,5-heptanedione metal complex by reacting the 2,6-dimethyl-3,5-heptanedione prepared as above with a metal salt.

It is a further object of the invention to provide a process for producing a metal or a metallic compound using the 2,6-dimethyl-3,5-heptanedione metal complex.

The present inventors have earnestly studied to solve such problems associated with the prior art as described above, and as a result, they have found that 2,6-dimethyl-3,5-heptanedione can be synthesized in the presence of an easily handled alkali metal alkoxide catalyst by reacting an alkyl isobutyrate with 3-methylbutanone using the alkyl isobutyrate as a solvent but using no other solvent in the beginning of the reaction or by reacting them in liquid amide or liquid urea. Based on the finding, the present invention has been accomplished.

Further, the present inventors have also found that by the reaction of the thus-prepared 2,6-dimethyl-3,5-heptanedione with a metal salt, a 2,6-dimethyl-3,5-heptanedione metal complex can be readily obtained.

SUMMARY OF THE INVENTION

That is to say, the present invention is as follows.

[1] A process for preparing a β-diketone compound represented by the following formula (3), comprising a step 1 of reacting an ester compound represented by the following formula (1) with a ketone compound represented by the following formula (2) in the presence of an alkali metal alkoxide catalyst, $$CR^1R^2R^3COOQ \qquad (1)$$

wherein $R^1$ to $R^3$ are each independently hydrogen or an alkyl group of 1 to 3 carbon atoms, and Q is an alkyl group, $$CR^4R^5R^6COCH_2R^7 \qquad (2)$$

wherein $R^4$ to $R^6$ are each independently hydrogen or an alkyl group of 1 to 3 carbon atoms, and $R^7$ is hydrogen or an alkyl group of 1 to 4 carbon atoms, $$CR^1R^2R^3COCHR^7COCR^4R^5R^6 \qquad (3)$$

wherein $R^1$ to $R^7$ have the same meanings as defined above and at least one of $R^1$ to $R^6$ is hydrogen.

[2] The process as described in [1], wherein at least one compound selected from an ester compound represented by the following formula (1), liquid amide and liquid urea is used as a solvent, $$CR^1R^2R^3COOQ \qquad (1)$$

wherein $R^1$ to $R^3$ are each independently hydrogen or an alkyl group of 1 to 3 carbon atoms, and Q is an alkyl group.

[3] The process as described in [1], wherein the compound represented by the formula (1) is an alkyl isobutyrate, the compound represented by the formula (2) is 3-methylbutanone, and the compound represented by the formula (3) is 2,6-dimethyl-3,5-heptanedione.

[4] The process as described in [3], wherein the reaction is carried out using the alkyl isobutyrate as a solvent and using no other solvent.

[5] The process as described in [3], wherein liquid amide or liquid urea is used as a solvent.

[6] The process as described in [5], wherein the solvent is at least one solvent selected from N,N-dimethylformamide, N,N-dimethylacetamide, N-methylpyrrolidone and 1,3-dimethyl-2-imidazolidinone.

[7] The process as described in [6], wherein the solvent is N,N-dimethylformamide and/or 1,3-dimethyl-2-imidazolidinone.

[8] The process as described in any one of [4] to [7], wherein the amount of the solvent used is in the range of 3 to 30 times by mass based on the 3-methylbutanone.

[9] The process as described in any one of [3] to [7], wherein the alkali metal of the alkali metal alkoxide catalyst is sodium or potassium.

[10] The process as described in [9], wherein the alcohol portion of the alkali metal alkoxide catalyst is a tertiary alcohol.

[11] The process as described in any one of [3] to [7], wherein the amount of the alkali metal alkoxide catalyst used is in the range of 1 to 10 times by mol based on the 3-methylbutanone.

[12] The process as described in [3], comprising a step 1 of synthesizing 2,6-dimethyl-3,5-heptanedione by reacting the alkyl isobutyrate with the 3-methylbutanone in the presence of the alkali metal alkoxide catalyst and a step 2 of adding an acid to the reaction solution of 2,6-dimethyl-3,5-heptanedione to perform neutralization and adding water to the solution to separate the solution into two layers and thereby isolate the 2,6-dimethyl-3,5-heptanedione as an oil layer.

[13] The process as described in [12], wherein the acid is at least one acid selected from sulfuric acid, hydrochloric acid and nitric acid.

[14] The process as described in [12] or [13], comprising recovering the alkyl isobutyrate, 3-methylbutanone and the solvent from the oil layer containing 2,6-dimethyl-3,5-heptanedione by distillation separation and reusing them in the reaction.

[15] A process for preparing a 2,6-dimethyl-3,5-heptanedione metal complex, comprising a step 3 of reacting the 2,6-dimethyl-3,5-heptanedione obtained in the process as described in [12] with a metal salt.

[16] The process as described in [15], wherein the metal salt is at least one metal salt selected from the group consisting of a halide, a nitrate, a sulfate and a phosphate of a metal.

[17] The process as described in [16], wherein the metal salt is a chloride of a metal and/or a nitrate of a metal.

[18] The process as described in [15], wherein the metal of the metal salt is at least one metal selected from transition metals and alkaline earth metals.

[19] The process as described in [18], wherein the metal is at least one metal selected from alkaline earth metals, rare earth metals, Ti, Zr, Hf and Cu.

[20] The process as described in [15], wherein a hydrophilic solvent is used as a solvent in the reaction of the 2,6-dimethyl-3,5-heptanedione with the metal salt.

[21] The process as described in [20], wherein the hydrophilic solvent is an alcohol of 1 to 4 carbon atoms.

[22] The process as described in [21], wherein the alcohol is methanol.

[23] The process as described in [15], wherein after the reaction is completed, water is added to precipitate the 2,6-dimethyl-3,5-heptanedione metal complex, followed by isolating the metal complex.

[24] The process as described in any one of [15] to [23], wherein the 2,6-dimethyl-3,5-heptanedione metal complex is a metal complex wherein 2 to 4 molecules of 2,6-dimethyl-3,5-heptanedione are coordinated to 1 atom of the metal.

[25] A process for preparing a metal or a metallic compound, in which the 2,6-dimethyl-3,5-heptanedione metal complex obtained in the step 3 of the process as described in [15] is used as a starting material.

[26] The process as described in [25], wherein the 2,6-dimethyl-3,5-heptanedione metal complex is used in a vaporized form.

[27] The process as described in [26], which involves chemical vapor deposition.

[28] The process as described in any one of [25] to [27], wherein the metal or the metallic compound produced is a metal oxide.

[29] The process as described in [28], wherein the metal oxide produced is a metal oxide film.

DETAILED DESCRIPTION OF THE INVENTION

The present invention is described in detail hereinafter.

One of the characteristic features of the present invention is to prepare a β-diketone compound represented by the following formula (3) by reacting an ester compound represented by the following formula (1) with a ketone compound represented by the following formula (2) in the presence of an alkali metal alkoxide catalyst, $$CR^1R^2R^3COOQ \qquad (1)$$

wherein $R^1$ to $R^3$ are each independently hydrogen or an alkyl group of 1 to 3 carbon atoms, and Q is an alkyl group, $$CR^4R^5R^6COCH_2R^7 \qquad (2)$$

wherein $R^4$ to $R^6$ are each independently hydrogen or an alkyl group of 1 to 3 carbon atoms, and $R^7$ is hydrogen or an alkyl group of 1 to 4 carbon atoms, $$CR^1R^2R^3COCHR^7COCR^4R^5R^6 \quad (3)$$

wherein $R^1$ to $R^7$ have the same meanings as defined above and at least one of $R^1$ to $R^6$ is hydrogen.

The β-diketone compound will be discussed in detail hereinbelow taking as an example particularly useful 2,6-dimethyl-3,5-heptanedione.

The preferred process of the invention is a process for preparing 2,6-dimethyl-3,5-heptanedione from an alkyl isobutyrate and 3-methylbutanone in an organic solvent using an alkali metal alkoxide catalyst. The alkyl isobutyrate for use in the invention has a structure of the formula (1) wherein two of $R^1$ to $R^3$ are each a methyl group and the other is hydrogen, and Q that is an alcohol portion of the ester is not specifically restricted provided that it is an alkyl group. Q is preferably an alkyl group of 1 to 6 carbon atoms. Examples of such alkyl isobutyrates include methyl isobutyrate, ethyl isobutyrate, isopropyl isobutyrate and butyl isobutyrate.

To produce β-diketone compounds other than the 2,6-dimethyl-3,5-heptanedione, the compound having the formula (1) may be selected from the alkyl isobutyrates and other compounds such as methyl propionate, ethyl propionate, methyl acetate, ethyl acetate, methyl pivalate and methyl valerate.

When Q is a phenyl group, the reactivity of the ester is enhanced, but since the acidity of the phenol liberated is strong, the phenol reacts with the catalyst to form an alkali metal phenoxide that is low-alkaline, and as a result, the reaction is markedly inhibited.

The 3-methylbutanone as a starting material is not specifically restricted, and any of commercially available ones is employable.

To produce β-diketone compounds other than the 2,6-dimethyl-3,5-heptanedione, the compound of the formula (2) may be selected from the 3-methylbutanone and others including pinacolone(3,3-dimethyl-2-butanone), methyl ethyl ketone, methyl propyl ketone and methyl isopropyl ketone.

In the reaction of the invention, the reactivity greatly varies depending upon the solvent used. It is possible that in the beginning of the reaction, particularly no solvent is employed and the alkyl isobutyrate is used in large amounts to work as solvent.

Of the solvents other than the alkyl isobutyrate, liquid amide or liquid urea can effectively promote the reaction. The liquid amide is a compound that is liquid under the reaction conditions and has an amide bond, such as N,N-dimethylformamide (DMF), N,N-dimethylacetamide (DMAc) or N-methyl-2-pyrrolidone (NMP). The liquid urea is a compound which is liquid under the reaction conditions and has a urea bond, such as 1,3-dimethyl-2-imidazolidinone (DMI). Particularly, DMF and DMI are preferable because hydrogen is not present at the α-position relative to the carbonyl group and any carboanion is not generated, and therefore side reaction due to the condensation reaction of carboanion with ketone or ester can be inhibited. These solvents can be used singly or as a mixture of two or more kinds. It is possible to use other solvents in combination as far as no adverse effects are caused to the reaction (for example, solvents which will act on or react with the alkali metal alkoxide catalyst cannot be used). However, if a solvent other than the liquid amide or liquid urea is used alone, the reactivity is markedly lowered.

If the solvent used contains water, the reaction is inhibited, so that it is desirable to dehydrate the solvent prior to use.

The lower limit of the amount of the alkyl isobutyrate used as the solvent or the amount of the liquid amide or liquid urea is not specifically restricted as far as stirring of the reaction system is feasible. Although the upper limit thereof is not specifically restricted, too dilute reaction system lowers productivity or reactivity and is unfavorable. Therefore, the solvent is preferably used, on the basis of mass, in an amount of 0 to 50 times by mass, more preferably 1 to 40 times by mass, and particularly preferably 1 to 30 times by mass based on the 3-methylbutanone. On the basis of mol, the solvent is preferably used in an amount of 0 to 70 times by mol, more preferably 0.2 to 50 times by mol, and particularly preferably 0.5 to 20 times by mol based on the 3-methylbutanone.

The amount of the alkyl isobutyrate used for the reaction is in the range of 0.5 to 10 times by mol, preferably 1 to 5 times by mol, and more preferably 1.1 to 3 times by mol based on the 3-methylbutanone. If the amount of the 3-methylbutanone is excessively larger than that of the alkyl isobutyrate, the yield is lowered by the great influence of self-condensation of the 3-methylbutanone. If the amount of the alkyl isobutyrate is excessively larger than that of the 3-methylbutanone, a large amount of the unreacted alkyl isobutyrate must be recovered. However, when the alkyl isobutyrate is used as the solvent, the alkyl isobutyrate used as the starting material and the alkyl isobutyrate used as the solvent are not differentiated in the reaction system, so that the alkyl isobutyrate is used in an amount of 10 to 30 times by mass based on the 3-methylbutanone.

There is no specific limitation on the method of addition of the alkyl isobutyrate and the 3-methylbutanone, and it is possible to introduce them in the reactor all at once prior to the initiation of the reaction, or to feed the 3-methylbutanone first and then add the alkyl isobutyrate slowly, or to add the alkyl isobutyrate and the 3-methylbutanone at the same time. However, in order to prevent self-condensation of the 3-methylbutanone, it is preferable to feed the alkyl isobutyrate previously and then add the 3-methylbutanone slowly so that the amount of the alkyl isobutyrate should exceed the amount of the 3-methylbutanone in the reaction solution. The alkyl isobutyrate and the 3-methylbutanone may be added as they are, or they may be added after dissolved in the solvent used.

The reaction temperature is desired to be in the range of 0 to 150° C., preferably 20 to 100° C. If the reaction temperature is too low, the reactivity becomes worse and the reaction time is prolonged, resulting in low productivity. If the reaction temperature is too high, the yield is lowered by the influences of decomposition of the solvent due to alkali and progress of side reaction.

As the alkali metal alkoxide catalyst for use in the reaction, any compound is employable, but the alkali metal is preferably sodium or potassium, more preferably potassium. As the alcohol for forming the alkoxide, a monohydric alcohol having an alkyl group of 1 to 6 carbon atoms which may be branched is usually used, but a polyhydric alcohol (e.g., ethylene glycol or propylene glycol) or an alkoxy alcohol wherein a part of the carbon chain of the alkyl group is substituted with oxygen (e.g., monoalkyl ether of ethylene glycol) may be used. Preferable is a tertiary alcohol having an alkyl group. For example, tert-butoxypotassium can be mentioned.

The alkali metal alkoxide catalysts mentioned above may be used singly or in combination of two or more kinds in an arbitrary proportion. If the amount of the base added is too small, the reactivity becomes worse. If the amount thereof is too large, the yield is lowered by decomposition of the solvent due to alkali or side reaction. The amount of the base is preferably in the range of 1 to 10 mol based on 1 mol of the 3-methylbutanone.

When Claisen condensation reaction of the alkyl isobutyrate with the 3-methylbutanone is carried out in the presence of the alkali metal alkoxide catalyst to synthesize 2,6-dimethyl-3,5-heptanedione, the resulting 2,6-dimethyl-3,5-heptanedione is present as an alkyl metal salt. In order to isolate the 2,6-dimethyl-3,5-heptanedione, the alkali metal salt of 2,6-dimethyl-3,5-heptanedione is neutralized with an acid and thereby freed.

Examples of the acids used herein include mineral acids, such as hydrochloric acid, sulfuric acid, nitric acid and phosphoric acid; organic acids, such as formic acid and acetic acid; and Lewis acids, such as ferrous chloride, ferric chloride, stannous chloride and aluminum chloride. Preferably used are sulfuric acid, hydrochloric acid and nitric acid. These acid components may be used singly or in combination of two or more kinds in an arbitrary proportion. The amount of the acid added should be at least equivalent to that of the alkali metal alkoxide catalyst used for the reaction. Since the neutralization is an exothermic reaction, cooling may be carried out according to need.

In order to recover the 2,6-dimethyl-3,5-heptanedione formed by the reaction, water is added to the reaction solution to separate the solution into an oil layer consisting of the 2,6-dimethyl-3,5-heptanedione formed by the reaction, alkyl isobutyrate, 3-methylbutanone and solvent, and an aqueous layer consisting of water, solvent and inorganic salt. Since the 2,6-dimethyl-3,5-heptanedione has hydrophobic groups, it is hardly dissolved in water, so that the 2,6-dimethyl-3,5-heptanedione can be recovered in a good recovery ratio even if no extraction agent is used. However, hydrocarbon, ether, aromatic hydrocarbon or the like may be added for the extraction when needed.

The oil layer separated as above can be subjected to distillation purification when needed. The alkyl isobutyrate, 3-methylbutanone and the solvent having a lower boiling point than the aimed product can be readily recovered and reused for the reaction.

There is no specific limitation on the process to prepare a metal complex from the 2,6-dimethyl-3,5-heptanedione prepared by the process of the invention. For example, the metal complex can be prepared by the processes described in Inorganic Synthesis, 11 (1968) and Inorganic Synthesis, 31 (1997). Usually, the metal complex can be prepared by reacting the 2,6-dimethyl-3,5-heptanedione with a metal salt in an organic solvent.

The metal of the 2,6-dimethyl-3,5-heptanedione metal complex is not specifically restricted provided that it is a metal capable of forming a metal complex together with β-diketone. Preferred examples of such metals include alkaline earth metals, rare earth metals, Ti, Zr, Hf, Sn, Fe, Al, Mn, Co, Ni, Zn, Ga, Pd, Cd, In and Cu. Examples of the alkaline earth metals include Sr and Ba, and examples of the rare earth metals include Y, La, Pr, Nd, Sm, Eu, Tb and Tm.

The metal is preferably a metal being divalent to tetravalent ions in consideration of easy coordination of the 2,6-dimethyl-3,5-heptanedione molecules. When the metal ion is n-valent, n molecules of the 2,6-dimethyl-3,5-heptanedione are usually coordinated to one metal.

Although the metal salt used for the reaction with the 2,6-dimethyl-3,5-heptanedione is not specifically restricted, preferable is a salt of inorganic ion. Examples of such salts include halide, nitrate, sulfate, phosphate and perchlorate. Particularly preferable are nitrate and chloride. These salts may be used singly or as a mixture.

The quantity ratio between the metal salt and the 2,6-dimethyl-3,5-heptanedione varies depending upon the valence of the metal of the metal salt, and when the valence of the metal is n, it is preferable to use the 2,6-dimethyl-3,5-heptanedione in an amount of n×0.9 to n×1.5 times by mol.

As the solvent for the reaction of the 2,6-dimethyl-3,5-heptanedione with the metal salt, an organic solvent can be used without any restriction. The solvent is preferably a solvent capable of dissolving the metal salt. Therefore, preferable is a polar solvent, particularly a hydrophilic solvent, and more preferable is an alcohol type solvent having 1 to 4 carbon atoms. Examples of such solvents include methanol, ethanol, propanol, isopropanol, butanol, methoxyethanol and ethoxyethanol.

The reaction temperature is not lower than the melting point of the solvent and not higher than the boiling point thereof. When the reaction is carried out at a temperature in the vicinity of room temperature, any trouble is not brought about. Accordingly, the reaction temperature is in the range of preferably 10 to 40° C., particularly preferably 15 to 35° C.

When the solvent is hydrophobic, the 2,6-dimethyl-3,5-heptanedione metal complex formed by the reaction can be obtained by concentration. When the solvent is a hydrophilic solvent that is usually used, water is added to precipitate the metal complex as solids, and the solids can be isolated by filtration, centrifugation or the like. Depending upon the type of the metal, the metal complex is sometimes precipitated even if water is not particularly added.

The 2,6-dimethyl-3,5-heptanedione metal complex can be converted into a metal oxide by the chemical vapor deposition publicly known (e.g., the 4th edition Experimental Chemistry Lectures 13, p. 46). For example, the 2,6-dimethyl-3,5-heptanedione metal complex is vaporized, and the vapor is mixed with a gas containing oxygen and heated to give a metal oxide.

A typical example of such process is MOCVD. MOCVD is a general term for the technique wherein an organometallic compound as a starting material is thermally decomposed in the vicinity of a substrate to perform crystal growth, and this technique is now utilized for the formation of oxides such as compound semiconductors, magnetic substances, ferroelectric thin films and high-temperature superconductor crystals. More specifically, the substrate is heated in a vacuum reactor, then an organometallic compound gas and if desired oxygen are fed to the vicinity of the substrate, and thermal decomposition reaction is conducted on the substrate surface or in the vicinity of the substrate by induction heating due to high-frequency power or plasma generation to form a metal film or an oxide film on the substrate surface.

The β-diketone metal complex and its derivatives are conventional organometallic compounds known as starting materials in MOCVD. The decomposability and the evaporation temperatures of the organometallic compounds can be controlled by appropriately selecting the hydrocarbon group in the side chain of the β-diketone ligand.

EXAMPLE

The present invention is further described with reference to the following examples, but it should be construed that the invention is in no way limited to those examples.

Quantitative determination of β-diketone in the following examples was made by gas chromatography. The analytical conditions are described below. With regard to the β-diketone, a reagent having a purity of not less than 97% available from Tokyo Kasei Kogyo Co., Ltd. was used as a standard product of 97% purity.

Gas Chromatography Conditions

Apparatus: GC-14A manufactured by Shimadzu Seisakusho K.K., Split method (split ratio: 60)
Capillary Column: DB-5 manufactured by J&W Co., 0.25 mmø×30 m, stationary liquid thickness: 0.25μ
Carrier gas: helium
Injection quantity: 1 μl
INJ. temperature: 250° C.
DET. temperature (FID): 280° C.
Temperature program: 50° C.→5 min hold→heating up to 250° C. at 10 C./min
Quantitative determination method: internal standard method (internal standard substance: naphthalene)

Example 1

In a 1-liter four-necked flask, 103 g of DMF and 1.33 mol (149 g) of tert-butoxypotassium were placed, and they were heated up to 50° C. with stirring by a mechanical stirrer. Then, a liquid mixture consisting of 2.64 mol (307 g) of ethyl isobutyrate and 0.88 mol (75.6 g) of 3-methyl-2-butanone, was added by a dropping funnel over a period of 3 hours, followed by further stirring for 8 hours under heating. It was confirmed by gas chromatography that 2,6-dimethyl-3,5-heptanedione was produced in an amount of 0.68 mol (107 g) in the solution (yield: 77.3% (based on 3-methylbutanone)).

Examples 2 to 12

β-Diketones were synthesized by the procedure illustrated in Example 1, except that different ketons and esters as the starting materials were used (the starting materials were used in same molar amounts as in Example 1). Details are given in Table 1.

TABLE 1

| Exam- | Starting materials | | Product | |
|---|---|---|---|---|
| ple | Ester | Ketone | β-Diketone | Yield |
| 1 | Ethyl isobutyrate | 3-Methyl-2-butanone | 2,6-Dimethyl-3,5-heptanedione | 77% |
| 2 | Ethyl acetate | Pinacolone | 2,2-Dimethyl-3,5-hexanedione | 35% |
| 3 | Ethyl acetate | Methyl isopropyl ketone | 2-Methyl-3,5-hexanedione | 63% |
| 4 | Ethyl propionate | Pinacolone | 2,2-Dimethyl-3,5-heptanedione | 76% |
| 5 | Methyl propionate | Methyl isopropyl ketone | 2-Methyl-3,5-heptanedione | 55% |
| 6 | Methyl propionate | Methyl ethyl ketone | 3,5-Heptanedione | 45% |
| 7 | Ethyl acetate | Methyl ethyl ketone | 2,4-Hexanedione | 35% |
| 8 | Methyl butyrate | Pinacolone | 2,2-Dimethyl-3,5-octanedione | 48% |
| 9 | Methyl butyrate | Methyl isopropyl ketone | 2-Methyl-3,5-octanedione | 60% |
| 10 | Methyl butyrate | Methyl propyl ketone | 4,6-Nonanedione | 54% |
| 11 | Methyl pivalate | Methyl isopropyl ketone | 2,2,6-Trimethyl-3,5-heptanedione | 61% |
| 12 | Methyl valerate | Pinacolone | 2,2-Dimethyl-3,5-nonanedione | 50% |

Comparative Example 1

The reaction was carried out in the same manner as in Example 1, except that the ethyl isobutyrate was replaced with phenyl isobutyrate. As a result, 2,6-dimethyl-3,5-heptanedione was not produced.

Example 13

To the reaction solution containing 2,6-dimethyl-3,5-heptanedione synthesized in the same manner as in Example 1, 133.7 g of concentrated hydrochloric acid was added and then 773 g of water was further added, to separate the solution into two layers consisting of an oil layer and an aqueous layer. The oil layer was recovered and analyzed by GC. As a result, the recovery of 2,6-dimethyl-3,5-heptanedione was 99.5%.

Example 14

In 51.4 g of methanol, 14.5 g (0.081 mol) of a sodium methylate methanol solution of 30% purity was dissolved with stirring, and the resulting solution was cooled to room temperature. Then, 12.65 g (0.081 mol) of 2,6-dimethyl-3,5-heptanedione of 97% purity was added little by little. To the mixture, a solution obtained by dissolving 12.63 g (0.0268 mol) of $Y(NO_3)_3 \cdot 6H_2O$ of 81.3% purity (determined by quantitative analysis) in 63.2 g of methanol was added at a temperature of 25 to 28° C. over a period of 30 minutes. The reaction was conducted for 1 hour, and the crystals precipitated were filtered off. The separated crystals were subjected to recrystallization using ethyl butyrate as a solvent. Thus, 7.46 g (yield: 50.2%) of tris(2,6-dimethyl-3,5-heptanedionato)yttrium was obtained.

Example 15

In 178 g of methanol, 66.9 g (0.372 mol) of a sodium methylate methanol solution of 30% purity was dissolved, and the resulting solution was cooled to room temperature. Then, 66.0 g (0.377 mol) of 2,6-dimethyl-3,5-heptanedione of 88% purity was dropwise added with stirring. To the mixture, a solution obtained by dissolving 50.0 g (0.124 mol) of $Fe(NO_3)_3 \cdot 9H_2O$ of 99% purity in 12.0 g of methanol was added at a temperature of 25 to 28° C. over a period of 30 minutes. The reaction was conducted for 1 hour, and the crystals precipitated were filtered off. To the resulting solution, 400 g of water was dropwise added over a period of 1 hour and 30 minutes. After the dropwise addition was completed, stirring was performed for 1 hour. The resulting crystals were taken out by centrifugation and then dried. Thus, 62.0 g (yield: 95.9%) of tris(2,6-dimethyl-3,5-heptanedionato)iron was obtained.

Example 16

To 300 g of methanol, 77.1 g (0.429 mol) of 2,6-dimethyl-3,5-heptanedione of 87% purity was dropwise added with stirring. To the resulting solution, a solution, which had been obtained by dissolving 25.0 g (0.106 mol) of $ZrCl_4$ of 99% purity in 100 g of methanol and cooled to room temperature, was dropwise added over a period of about 5 minutes. The reaction was conducted for 1 hour with stirring, and 1000 g of water was added over a period of 1 hour. Then, stirring was performed for 1 hour. The resulting solution was adjusted to pH 6.6 with a 20% NaOH solution. The resulting crystals were collected by centrifugation and then dried. Thus, 74.5 g (yield: 97.5%) of tetrakis(2,6-dimethyl-3,5-heptanedionato)zirconium was obtained.

Example 17

In 20 g of methanol, 7.20 g (0.0400 mol) of a sodium methylate methanol solution of 30% purity was dissolved, and the resulting solution was cooled to room temperature.

Then, 7.19 g (0.0400 mol) of 2,6-dimethyl-3,5-heptanedione of 87% purity was dropwise added with stirring. Then, 4.83 g (0.0300 mol) of $Cu(NO_3)_2 \cdot 6H_2O$ was added. After the reaction was conducted for 1 hour, 100 g of water was added over a period of 30 minutes, followed by stirring for 1 hour. The resulting crystals were filtered off and dried. Thus, 7.23 g (yield: 88.2%) of bis(2,6-dimethyl-3,5-heptanedionato)copper was obtained.

Example 18 and Comparative Example 2

$Y(DMHD)_3$ produced in Example 11 was formed into a $Y_2O_3$ film by MOCVD (Example 18). For comparison, a film was produced from $Y(DPM)_3$ (Comparative Example 2). (DPM: 2,2,6,6-tetramethyl-3,5-heptanedione, another name: dipivaloylmethane) Detailed are presented below.

The complexes as starting materials were each dissolved in methanol to achieve 20 wt % concentration and fed to a vaporizer through a constant rate pump.

$Y(DMHD)_3$ and $Y(DPM)_3$ were supplied at rates that gave equimolar amounts per hour.

The conditions in MOCVD are as follows:
Carrier gas: nitrogen
Vaporizer temperature: 250° C.
Substrate: Si (100)
Film-production time: 25 minutes With the substrate temperature set at 350° C., the material $Y(DMHD)_3$ gave a 450 nm thick $Y_2O_3$ film. Film production from the material $Y(DPM)_3$ under the same condition resulted in a 150 nm thick $Y_2O_3$ film.

At the substrate temperature of 300° C., $Y(DMHD)_3$ produced a $Y_2O_3$ film, while $Y(DPM)_3$ failed to form a $Y_2O_3$ film. This provided that DMHD can produce films at lower temperatures.

EFFECT OF THE INVENTION

According to the present invention, it becomes possible to use as a catalyst an alkali metal alkoxide that is easy to handle, and 2,6-dimethyl-3,5-heptanedione can be prepared under mild conditions at a low cost without necessity to invest a large sum of money in plant and equipment.

The 2,6-dimethyl-3,5-heptanedione prepared by the invention can be coordinated to a metal to synthesize a complex, and hence a 2,6-dimethyl-3,5-heptanedione metal complex that is a starting material for MOCVD can be provided at a low cost.

The invention claimed is:

1. A process for preparing a β-diketone compound represented by the following formula (3), comprising a step 1 of reacting an ester compound represented by the following formula (1) with a ketone compound represented by the following formula (2) in the presence of an alkali metal alkoxide catalyst, in at least one solvent selected from liquid amide having no hydrogen at the α-position relative to the carbonyl group and liquid urea having no hydrogen at the α-position relative to the carbonyl group, $$CR^1R^2R^3COOQ \qquad (1)$$

wherein $R^1$ to $R^3$ are each independently hydrogen or an alkyl group of 1 to 3 carbon atoms, and Q is an alkyl group, $$CR^4R^5R^6COCH_2R^7 \qquad (2)$$

wherein $R^4$ to $R^6$ are each independently hydrogen or an alkyl group of 1 to 3 carbon atoms, and $R^7$ is hydrogen or an alkyl group of 1 to 4 carbon atoms, $$CR^1R^2R^3COCHR^7COCR^4R^5R^6 \qquad (3)$$

wherein $R^1$ to $R^7$ have the same meanings as defined above and at least one of $R^1$ to $R^6$ is hydrogen.

2. The process as claimed in claim 1, wherein the compound represented by the formula (1) is an alkyl isobutyrate, the compound represented by the formula (2) is 3-methylbutanone, and the compound represented by the formula (3) is 2,6-dimethyl-3,5-heptanedione.

3. The process as claimed in claim 2, wherein the solvent is N,N-dimethylformamide and/or 1,3-dimethyl-2-imidazolidinone.

4. The process as claimed in claim 2, wherein the amount of the solvent used is in the range of 3 to 30 times by mass based on the 3-methylbutanone.

5. The process as claimed in claim 2, wherein the alkali metal of the alkali metal alkoxide catalyst is sodium or potassium.

6. The process as claimed in claim 5, wherein the alcohol portion of the alkali metal alkoxide catalyst is a tertiary alcohol.

7. The process as claimed in claim 2, wherein the amount of the alkali metal alkoxide catalyst used is in the range of 1 to 10 times by mol based on the 3-methylbutanone.

8. The process as claimed in claim 2, comprising a step 1 of synthesizing 2,6-dimethyl-3,5-heptanedione by reacting the alkyl isobutyrate with the 3-methylbutanone in the presence of the alkali metal alkoxide catalyst and a step 2 of adding an acid to the reaction solution of 2,6-dimethyl-3,5-heptanedione to perform neutralization and adding water to the solution to separate the solution into two layers and thereby isolate the 2,6-dimethyl-3,5-heptanedione as an oil layer.

9. The process as claimed in claim 8, wherein the acid is at least one acid selected from sulfuric acid, hydrochloric acid and nitric acid.

10. The process as claimed in claim 8, comprising recovering the alkyl isobutyrate, 3-methylbutanone and the solvent from the oil layer containing 2,6-dimethyl-3,5-heptanedione by distillation separation and reusing them in the reaction.

* * * * *